(12) United States Patent
Patterson et al.

(10) Patent No.: US 12,201,333 B1
(45) Date of Patent: *Jan. 21, 2025

(54) AUGMENTED SPANNING FIXATION BONE PLATE ASSEMBLY

(71) Applicant: Avanti Orthopaedics LLC, Newark, DE (US)

(72) Inventors: John Douglas Patterson, Wilmington, DE (US); Cyrus B. Gooray, Needham, MA (US); Meredith Nita Osterman, Wayne, PA (US); Devanand Gooray, Penn Valley, PA (US); A. Lee Osterman, Villanova, PA (US)

(73) Assignee: Avanti Orthopaedics LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/600,779

(22) Filed: Mar. 11, 2024

Related U.S. Application Data

(63) Continuation of application No. 17/948,197, filed on Sep. 19, 2022, now Pat. No. 11,925,395, which is a continuation of application No. 17/493,958, filed on Oct. 5, 2021, now Pat. No. 11,452,552.

(60) Provisional application No. 63/185,377, filed on May 7, 2021.

(51) Int. Cl.
*A61B 17/80* (2006.01)
*A61B 17/00* (2006.01)

(52) U.S. Cl.
CPC ...... *A61B 17/8023* (2013.01); *A61B 17/8061* (2013.01); *A61B 17/8085* (2013.01); *A61B 2017/00871* (2013.01)

(58) Field of Classification Search
CPC .................. A61B 17/8023; A61B 17/8061
See application file for complete search history.

(56) References Cited

U.S. PATENT DOCUMENTS

| | | | |
|---|---|---|---|
| 10,517,657 B1 | 12/2019 | Patterson | |
| 2008/0012245 A1 | 1/2008 | Peters | |
| 2010/0026219 A1 | 10/2010 | Michael et al. | |
| 2010/0262194 A1* | 10/2010 | Wagner | A61B 17/80 606/286 |
| 2018/0098802 A1* | 4/2018 | Ananthan | A61B 17/8057 |

* cited by examiner

*Primary Examiner* — Si Ming Ku
(74) *Attorney, Agent, or Firm* — Invention To Patent Services; Alex Hobson

(57) ABSTRACT

An augmented spanning fixation bone plate assembly combines an augmentation fixation bone plate with a spanning fixation bone plate. The augmentation fixation bone plate may be detachably attachable to the spanning fixation bone plate and may be slidably engaged with the spanning fixation bone plate to allow the augmentation fixation bone plate to be positioned for augmented fixation, wherein one or more separate bones are fixed with respect to the spanning fixation bone plate. An augmentation fixation bone plate may have one or more wings that extend laterally from the spanning fixation bone plate. An augmentation fixation bone plate may have two wings that extend in opposing lateral directions from the spanning fixation bone. A wing has a fastener aperture that may be slotted and may have an insert to enable directional fixation, wherein the fastener extends in an offset angle.

20 Claims, 8 Drawing Sheets

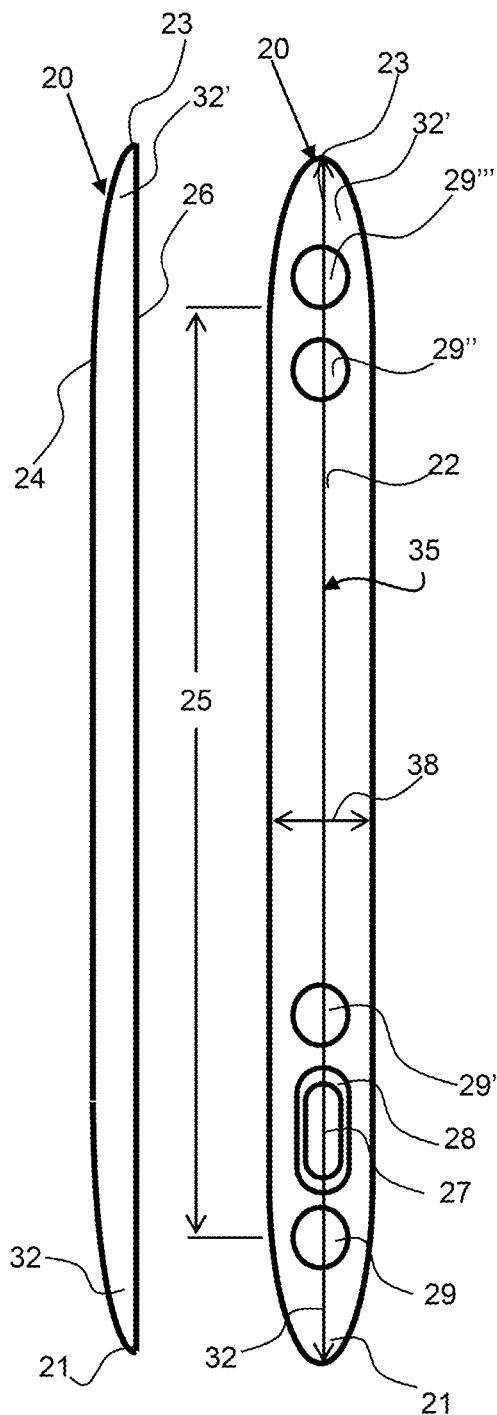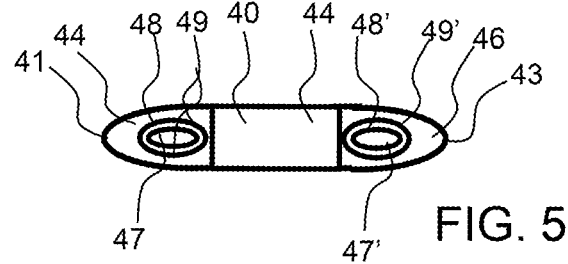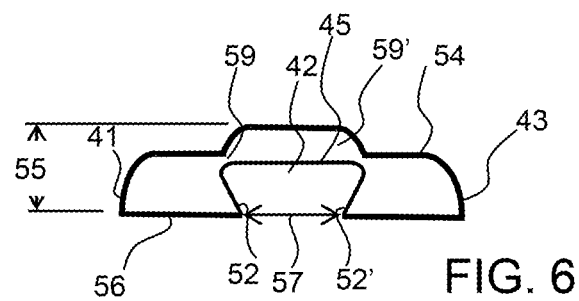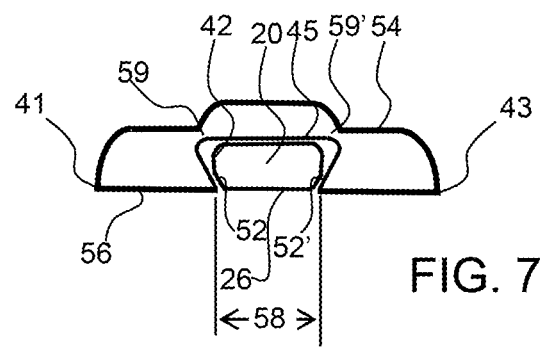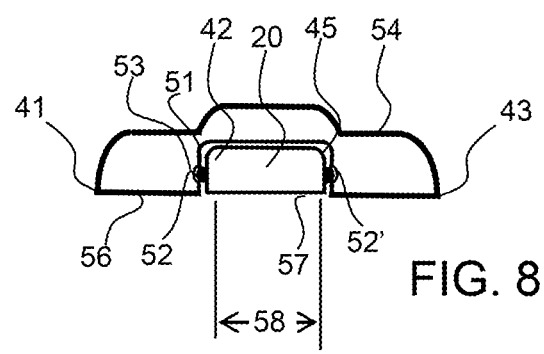
FIG. 3  FIG. 4

AUGMENTED SPANNING FIXATION BONE PLATE ASSEMBLY

CROSS REFERENCE TO RELATED APPLICATIONS

This application is a continuation of U.S. patent application Ser. No. 17/948,197 filed on Sep. 19, 2022 and currently pending, which is a continuation of U.S. patent application Ser. No. 17/493,958, filed on Oct. 5, 2021 and issued as U.S. patent Ser. No. 11/452,552 on Sep. 27, 2022, which claims the benefit of priority to U.S. provisional patent application No. 63/185,377, filed on May 7, 2021; the entirety of which is hereby incorporated by reference herein.

BACKGROUND OF THE INVENTION

Field of the Invention

The invention relates to an augmented spanning fixation bone plate assembly that combines an augmentation fixation bone plate that is slidably engaged with a spanning bone plate to enable fixation of other bones, such as in the hand, wrist or foot.

Background

Injuries of the hand, foot or wrist can be complex as more than one bone can be fractured and/or displaced. A spanning plate can be used to span the joint to neutralize forces across the area of injury. However, direct, rigid fixation of the spanned bones with such plates is not usually possible. This can lead to improper healing, loss of mobility and function and pain for the patient.

SUMMARY OF THE INVENTION

The invention is directed to an augmented spanning fixation bone plate assembly that combines an augmentation fixation bone plate with a spanning fixation bone plate. The augmentation fixation bone plate may be detachably attachable to the spanning fixation bone plate and may be slidably engaged with the spanning fixation bone plate to allow the augmentation fixation bone plate to be positioned for augmented fixation, wherein one or more separate bones are fixed with respect to the spanning fixation bone plate. An augmentation fixation bone plate may have one or more wings that extend laterally from the spanning fixation bone plate. In an exemplary embodiment, an augmentation fixation bone plate has two wings that extend in opposing lateral directions from the spanning fixation bone plate. Lateral, as used herein with reference to augmentation fixation bone plate extension from the spanning fixation bone plate, means to the side of, or outward from the spanning fixation bone plate, wherein the augmentation fixation bone plate extends generally orthogonally from the length axis of the spanning fixation bone plate, or within about 45 degrees of orthogonal, or within about 20 degrees of orthogonal.

An exemplary augment fixation bone plate may be detachably attachable to the spanning fixation bone plate, wherein interface surfaces of the augmentation fixation bone plate retain the augmentation fixation bone plate to the spanning fixation bone plate. An augmentation fixation bone plate may be pressed down onto the spanning fixation bone plate and flex outward to engage the interface surfaces. An attachment portion of the augmentation fixation bone plate may extend over or around at least a portion the spanning fixation bone plate thereby producing interfaces surfaces with the spanning fixation bone plate to retain the spanning fixation bone plate within the augmentation fixation bone plate. In an exemplary embodiment, the attachment portion of the augmentation fixation bone plate includes a retention aperture that forms a through hole in the augmentation fixation bone plate for receiving the spanning fixation bone plate. The retention surface in this embodiment is the boundary around the retention aperture or through hole in the attachment portion of the augmentation fixation bone plate.

An exemplary augmentation fixation bone plate may have a slot type retention aperture that is configured to be configured around the spanning fixation bone plate, such as around the side and the top of the spanning fixation bone plate. The slot type retention aperture has an insert opening that may open slightly through flexing of the augmentation fixation bone plate to snap the augmentation fixation bone plate onto the spanning fixation bone plate. The insert opening may be configured along the bone surface of the augmentation fixation bone plate and may have a width that is slightly less than the width of the spanning fixation bone plate over the body portion, such as about no more than 1 mm less, no more than about 2 mm less, no more than about 3 mm less and any range between and including the values provided. The interface surfaces may be planar surfaces that slide along planar surfaces of the spanning fixation bone plate or the interface surfaces may be contoured and match in contour to provide a secure engagement between the spanning fixation bone plate and the augmentation fixation bone plate. The slot type retention aperture in the augmentation fixation bone plate may produce a flexure portion of the augmentation fixation bone plate, a relatively thin section of the augmentation fixation bone plate between the top corners of the retention aperture and the top of the augmentation fixation bone plate, which may enable easier flexing and opening of the insert opening for press fitting the augmentation fixation bone plate onto the spanning fixation bone plate. A flexure portion may be much thinner than the thickness of the augmentation fixation bone plate, such as no more than a half of the thickness, no more than a third of the thickness, no more than a quarter of the thickness, no more than a fifth of the thickness and any range between and including the thickness ratios provided. The thickness of the flexure portion is the thinnest distance from the retention aperture and the top of the augmentation fixation bone plate and may be measure at an angle.

An interface surface may comprise a ball and detent arrangement with one of the ball or detent in the augmentation fixation bone plate and the other in the spanning fixation bone plate. Again, the augmentation fixation bone plate may be pressed down onto the spanning fixation bone plate to configure the ball within the detent and then the ball and detent form a slidably engaged interface surface.

An exemplary augmentation fixation bone plate system may be used for any suitable bone fixation procedure but may be particularly useful for fixation of bones in the hand, wrist or foot. In an exemplary embodiment, the augmentation fixation bone plate system is used for fixation of a fractured wrist, wherein the spanning fixation plate extends from the radius to one of the metacarpal bones and across the carpal bones. In some injuries, the carpal bones may be fractured and/or misaligned and the augmentation fixation bone plate may be used to secure one or more of the carpal bones in a desired position for bone fracture repair. Note that one wing may be used to secure one carpal bone in pace while the opposing wing, extending on an opposing side of the spanning fixation plate, is used to secure a second carpal bone in a desired position. Fasteners may be used and may extend through a fastener aperture in the wing or wings of the augmentation fixation bone plate.

An exemplary fastener aperture of an augmentation fixation bone plate may be a hole for receiving a screw and it may be a circular hole for directing a fastener directly down and through the fastener aperture and orthogonally to the wing extension from the spanning fixation bone plate. A fastener aperture may be slotted to allow for directional fixation, wherein the fastener is secured in an offset angle. A fastener aperture may have an insert that is a malleable material to allow head threads of a fastener to cut into the insert material for retention of the fastener in an offset angle. In an exemplary embodiment, a fastener aperture in the augmentation fixation bone plate is a slotted aperture with an insert to allow a wide range of direction and position options for securing a bone in a desired position. A fastener aperture may be a multi-aperture configured to receive two or more fasteners and may have a multi-aperture insert that is a malleable material as detailed herein. A multi-aperture insert may have a fastener divider that extends across the slotted aperture to provide addition material for the head thread to cut into for more positively securing the fastener in position. In some cases, the fastener may be used to move or reposition a bone, as required.

An exemplary augmentation fixation bone plate, and/or spanning fixation bone plate may be made out of metal, such as stainless steel, or titanium or may be made out of a polymeric material such as polyetheretherketone (PEEK), for example. A PEEK augmentation fixation bone plate may be more flexible and provide more flexure to enable the augmentation fixation bone plate to be more easily press fit down over a spanning fixation bone plate. In an exemplary embodiment, the spanning fixation bone plate is made of metal while the augmentation fixation bone plate is made of a polymeric material, including those listed herein.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

FIG. 3 shows a side view of an exemplary spanning fixation bone plate having load sharing extensions or tapering ends.

FIG. 4 shows a top view of an exemplary spanning fixation bone plate having a slotted aperture and a plurality of apertures for receiving a fastener therethrough to fix the spanning fixation bone plate to bone.

FIG. 5 shows a top view of an exemplary augmentation fixation bone plate having a pair of wings extending from an attachment portion, wherein the wings have slotted apertures with an insert to enable a fastener to be directionally fixed to through the aperture and into bone.

FIG. 6 shows a front view of the exemplary augmentation fixation bone plate shown in FIG. 5 with a retention aperture having interface surfaces configured to interface with the spanning fixation bone plate to enable slidable engagement of the augmentation fixation bone plate along the spanning fixation plate.

FIG. 7 shows a front view of the exemplary augmentation fixation bone plate shown in FIG. 6 with a spanning fixation bone plate configured in the retention aperture and retained by the interface surfaces.

FIG. 8 shows a front view of the exemplary augmentation fixation bone plate with a spanning fixation bone plate configured in the retention aperture and retained by the ball and detent interface surfaces.

Figure 1:
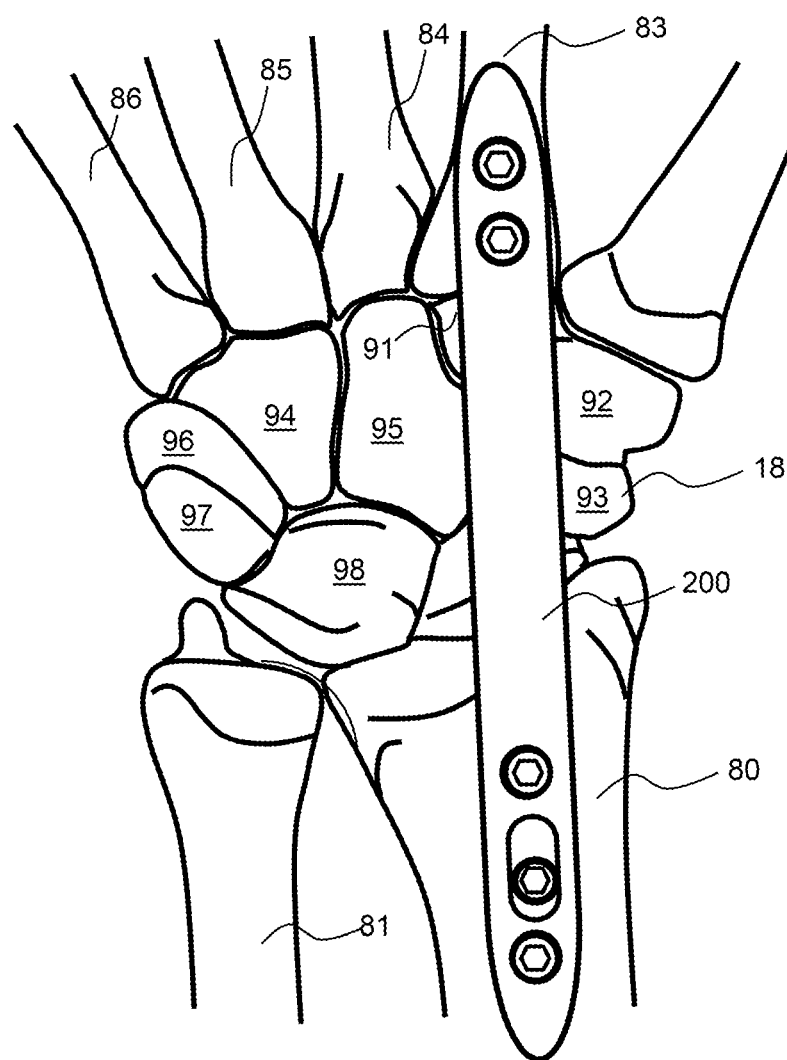
FIG. 1 shows a spanning fixation bone plate spanning across the wrist from the radius to the second metacarpal, thereby fixing the wrist.

Corresponding reference characters indicate corresponding parts throughout the several views of the figures. The figures represent an illustration of some of the embodiments of the present invention and are not to be construed as limiting the scope of the invention in any manner. Some of the figures may not show all of the features and components of the invention for ease of illustration, but it is to be understood that where possible, features and components from one figure may be included in the other figures. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1, a fixation bone plate 200 is spanning across the wrist from the radius 80 to the second metacarpal 83, thereby fixing the wrist 18. As described herein, some of the carpal bones may be fractured or out of place including the trapezoid 91, trapezium 92, scaphoid 93, hamate 94, capitate 95, triquetral 96, pisiform 97 and lunate 98. Furthermore, a spanning fixation bone plate may also extend from the ulna 81 across the wrist 18 to one of the metacarpal bones including, but not limited to, the first metacarpal 82, second metacarpal 83, third metacarpal 84, fourth metacarpal 85 and fifth metacarpal 86.

Figure 2:
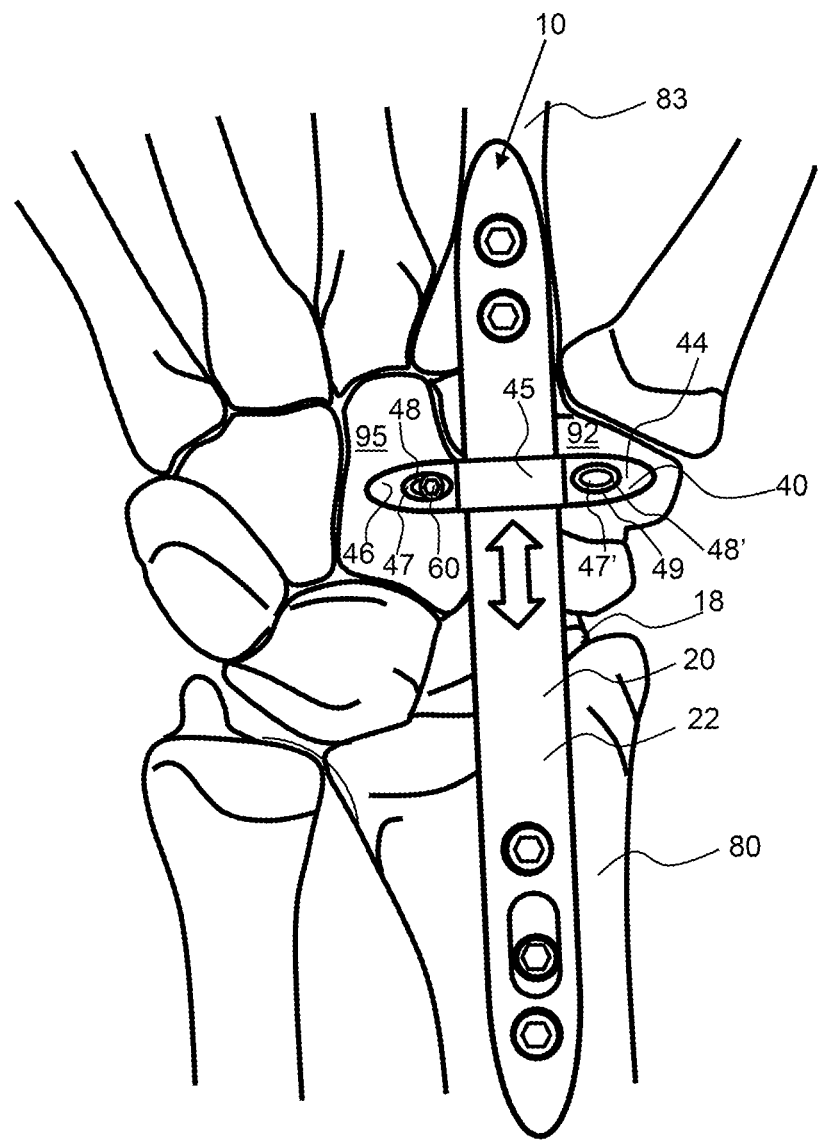
FIG. 2 shows an exemplary augmented spanning fixation bone plate assembly that includes the spanning fixation bone plate shown in FIG. 1 that spans the wrist from the radius to the second metacarpal, and an augmentation fixation bone plate that is slidably engaged with the spanning fixation bone plate and having wings extending laterally from the spanning fixation bone plate with fastener apertures to enable fixation of carpal bones in the wrist.

As shown in FIG. 2, an exemplary augmented spanning fixation bone plate assembly 10 includes a spanning fixation bone plate 20 that spans from the wrist, wherein it is attached to the radius 80 to the second metacarpal 83, and an augmentation fixation bone plate 40 that is slidably engaged with the spanning fixation plate. The augmentation fixation bone plate has an attachment portion 45 that is coupled with the spanning fixation bone plate and wings that extending laterally from the spanning fixation bone plate. Each of the first wing 44 and second wing 46 have a fastener aperture 49, such as a slotted fastener aperture 47 to enable fixation of carpal bones in the wrist. The slotted fastener apertures 47, 47' may have an insert 48, 48' to enable directional fixation of a fastener 60 to a bone, such as a carpal bone. As shown, a fastener 60 is directionally fixed through the slotted fastener aperture 47 and into the capitate 95 carpal bone.

With reference now to FIGS. 2 to 4, the spanning fixation bone plate 20 has a body portion 22 with a substantially uniform width 38 along the body portion length 25, to enable the augmented spanning fixation bone plate 40 to slide along the body portion. The width may vary but the interface surfaces may be uniform in width to enable a slidable engagement. The spanning fixation bone plate 20 has a length axis 35 that extends along the body portion length or from a first end 21 to a second end 23. The body portion length may be a substantial portion of the over length of the spanning fixation bone plate, such as about 60% or more, about 75% or more, about 80% of more, about 90% or more and any range between and including the percentages provided.

Referring now to FIGS. 3 and 4, an exemplary spanning fixation bone plate 20 has load sharing extensions 32, 32' extending to the first end 21 and second end 23, respectively. The load sharing extensions taper in both width and thickness to the ends of the spanning fixation plate. The spanning fixation bone plate has a slotted aperture 27 to enable the plate to be fixed to a bone, such as the ulna or radius and then slid into a desired position before fixing the plate with a faster through one of the remaining fastener apertures 29, 29', 29", and 29'". The slotted aperture or any of the other fastener apertures, may have an insert 28 to allow direction fixation with a fastener that extends in an offset angle. The spanning fixation bone plate 20 has a thickness from a top surface 24 to a bone surface 26. The spanning fixation bone plate 20 has a length axis 35 extending from the first end 21 to the second end 23.

Referring now to FIGS. 5 to 7, an exemplary augmentation fixation bone plate 40 has a length from a first end 41 to a second end 43 and a first wing 44 and a second wing 46 extending from an attachment portion 45. Each of the wings have fastener apertures 49, 49', such as a slotted fastener aperture 47, 47'. An insert 48, 48' may be configured in the fastener aperture to enable a fastener to be directionally secured through the insert and into bone, such as a carpal bone. As described herein, the insert may be a polymeric material that enables threads of a fastener to cut into the insert material to fix the fastener to the insert, including at an offset angle.

As shown in FIG. 6, the attachment portion 45 is centrally configured between the first wing 44 and the second wing 46 and has a retention aperture 42 with interface surfaces 52, 52' configured to interface with the spanning fixation bone plate to enable slidable engagement of the augmentation fixation bone plate along the spanning fixation bone plate and in particular along the along the body portion length 25, as shown in FIG. 4 as having a uniform width 38. The ends of the spanning fixation bone plate may be tapered to allow insertion of an end of the spanning fixation bone plate into the retention aperture of the augmentation fixation bone plate to enable the augmentation fixation bone plate to be slid down along the body portion length of the spanning fixation bone plate. The retention aperture has an insert opening 57 that is configured to extend over or around the spanning fixation bone plate as shown in FIG. 7. The width of the insert opening may be less than the width of the spanning fixation bone plate along the body portion. The augmentation fixation bone plate may be configured to slide over the spanning fixation bone plate or may be configured to flex and expand the insert opening width for extending over the spanning fixation bone plate. When the augmentation fixation bone plate 40 is configured over the spanning fixation bone plate 20, the insert opening width, may be less than the width 38 of the spanning fixation bone plate along the bone surface to retain the augmentation fixation bone plate 40 on the spanning fixation bone plate. Note that the spanning fixation bone plate may be configured to slide into the retention aperture 42 having the insert opening 57, instead of flexing to open the insert opening for insertion of the spanning fixation bone plate. As shown, the top surface 54 of the augmentation fixation bone plate is raised in the attachment portion but the bone surface 56 is planar, excluding the retention aperture.

As shown in FIG. 7, the exemplary augmentation fixation bone plate 40 shown in FIG. 6 now has a spanning fixation bone plate 20 configured in the retention aperture 42 and retained by the interface surfaces 52. The width 58 of the insert opening may be slightly less than the width 38 of the spanning fixation plate along the bone surface 26, shown in FIGS. 3 and 4, thereby requiring the augmentation fixation bone plate to flex slightly to couple the augmentation fixation bone plate around the spanning fixation plate, when the augmentation fixation bone plate is press fit down onto the spanning fixation bone plate. This slot type retention aperture 42 in the augmentation fixation bone plate may produce a flexure portion 59, 59' of the augmentation fixation bone plate, a relatively thin section of the augmentation fixation bone plate between the top corners of the retention aperture and the top of the augmentation fixation bone plate, which may enable easier flexing and opening of the insert opening 57 for press fitting the augmentation fixation bone plate onto the spanning fixation bone plate. The flexure portion has a thickness that is much less than the thickness 55 of the augmentation fixation bone plate or even the thickness of the wings of the augmentation fixation bone plate. The bone surface 26 of the spanning fixation bone plate 20, is substantially aligned, or planar with the bone surface 56 of the augmentation fixation bone plate 40, wherein these two surfaces or planes of these surfaces, are within about 4 mm of each other, or preferably within about 2 mm of each other, or within about 1 mm of each other and any range between and including the values provided. Attaching the augmentation fixation bone plate by press fitting down over the spanning fixation bone plate may be a preferred method as this may allow attachment of the spanning fixation bone plate to bone prior to attachment of the augmentation fixation bone plate by press fitting. A tool may also be used to expand the insert opening of the augmentation fixation bone plate for press fitting onto the spanning fixation bone plate.

As shown in FIG. 8, the exemplary augmentation fixation bone plate has a spanning fixation bone plate 20 configured in the retention aperture 42 and retained by the ball and detent interface surfaces 52, 52'. The ball 51 is extending from the spanning fixation bone plate and the detent 53 is in the augmentation fixation bone plate 40 but this relationship could be reversed.

Figure 9:
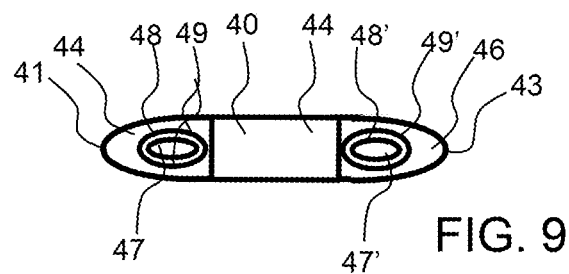
FIG. 9 shows a top view of an exemplary augmentation fixation bone plate having a pair of wings extending from an attachment portion, wherein the wings have slotted apertures with an insert to enable a fastener to be directionally fixed to through the aperture and into bone.
Figure 10:
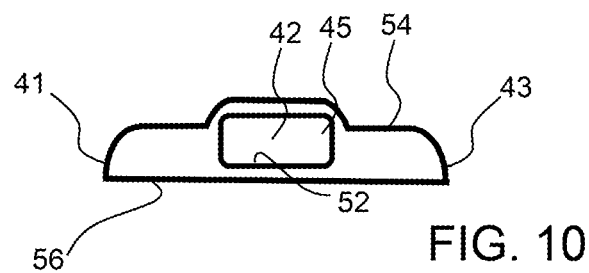
FIG. 10 shows a front view of the exemplary augmentation fixation bone plate shown in FIG. 9 with a retention aperture having an interface surface configured to interface with the spanning fixation bone plate to enable slidable engagement of the augmentation fixation bone plate along the spanning fixation plate.
Figure 11:
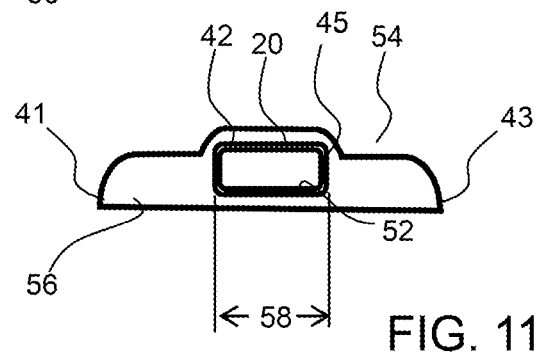
FIG. 11 shows a front view of the exemplary augmentation fixation bone plate shown in FIG. 10 with a spanning fixation bone plate configured in the retention aperture and retained by the interface surface.

Referring now to FIGS. 9 to 11, an exemplary augmentation fixation bone plate 40 has a length from a first end 41 to a second end 43 and a first wing 44 and a second wing 46 extending from an attachment portion 45. Each of the wings have fastener apertures 49, 49', such as a slotted fastener aperture 47, 47'. An insert 48, 48' may be configured in the fastener aperture to enable a fastener to be directionally secured through the insert and into bone, such as a carpal bone. As described herein, the insert may be a polymeric material that enables threads of a fastener to cut into the insert material to fix the fastener to the insert, including at an offset angle.

A shown in FIG. 10, the attachment portion 45 is centrally configured between the first wing 44 and the second wing 46 and has a retention aperture 42 forming an interface surface 52, configured to interface with the spanning fixation bone plate to enable slidable engagement of the augmentation fixation bone plate along the spanning fixation plate. In this embodiment, the retention aperture in an opening through the augmentation fixation bone plate 40.

As shown in FIG. 11, the exemplary augmentation fixation bone plate 40 shown in FIG. 10 now has a spanning fixation bone plate 20 configured in the retention aperture 42 and retained by the interface surfaces 52. The width 58 of the retention aperture may be slightly greater than the width 38 of the spanning fixation plate to enable insertion of the spanning fixation bone plate through the retention aperture.

Figure 12:
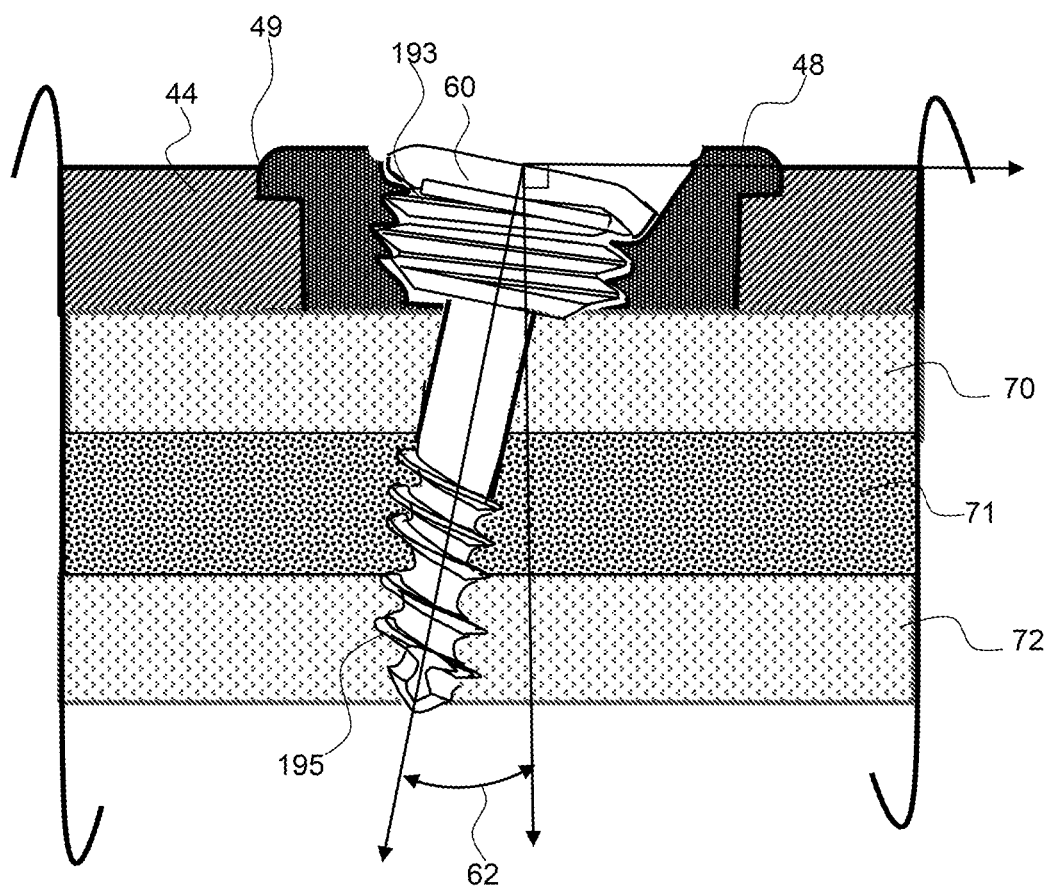
FIG. 12 shows a cross sectional view of a slotted aperture insert having a fastener retained at an offset angle by either the side of the slotted aperture insert.

As shown in FIG. 12, fastener 60 is secured into an insert 48 of a slotted aperture 49 in the first wing 44. The fastener has head threads 193 that cut into the insert material to secure the fastener to the insert at a directional angle 62 from orthogonal to the wing extension. The fastener has bone threads 195 configured on an extended end of the fastener that secure the fastener to the distal compact bone 72. Note that threads may also be configured to secure the fastener to the proximal compact bone 70 of the bone 71.

Figure 13:
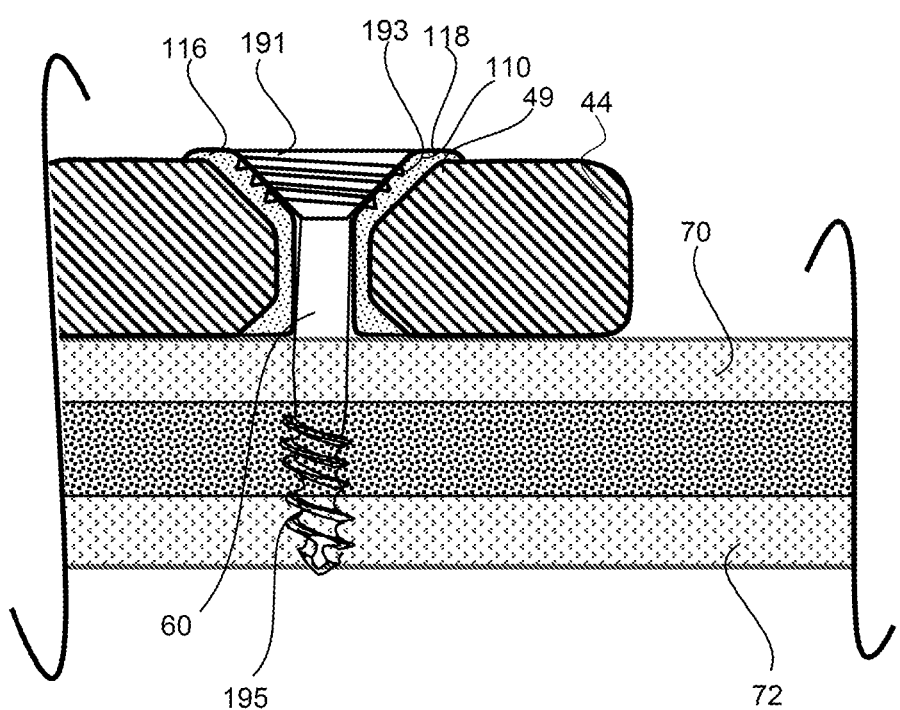
FIG. 13 shows a cross sectional view of an aperture with an insert and a fastener retained by the insert.

Referring now to FIGS. 13, the fastener 60 is retained by either side of a slotted aperture insert 116, which may be a multi-aperture inserts 110 configured to receive two or more fasteners therethrough. The slotted aperture insert has a beveled opening 118 and the fastener head 191 has head threads 193 that cut into the beveled opening portion of the multiple fastener slotted aperture insert. The fastener has bone threads 195 on the distal end that secure the fastener to the bone. The slotted aperture insert 116 may be press fit into a slotted aperture of the bone plate.

Figure 14:
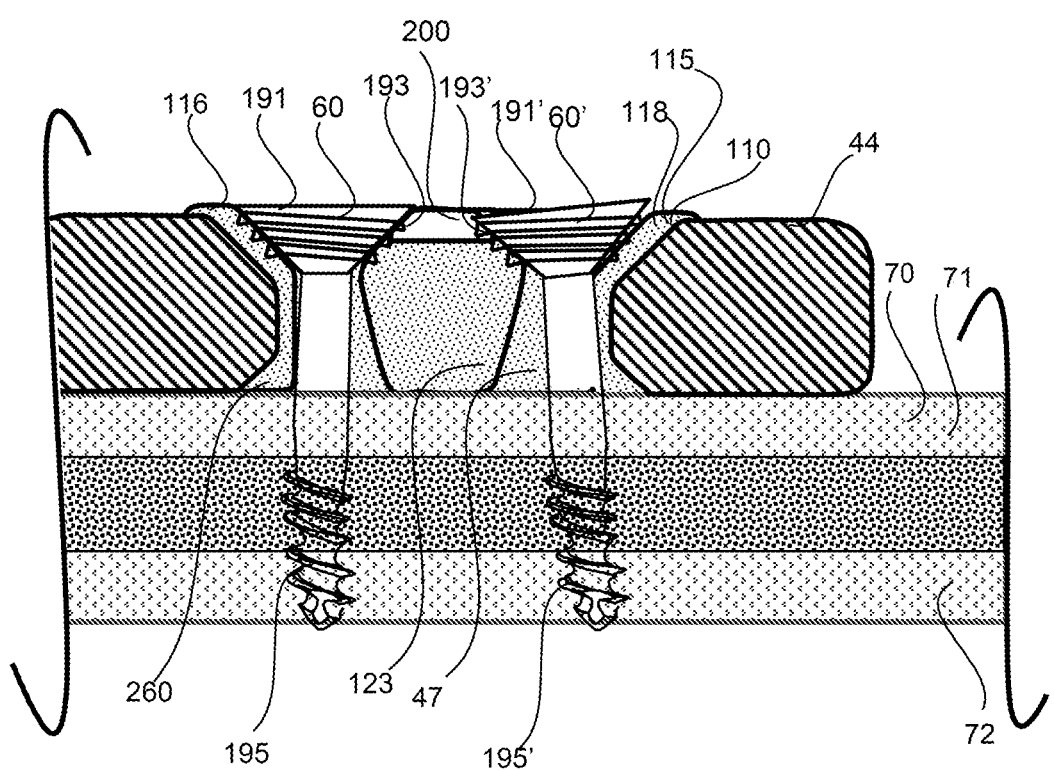
FIG. 14 shows a cross sectional view of a slotted aperture insert having a fastener divider and the two fasteners retained by either the side of the slotted aperture insert the end of the slotted aperture and the fastener divider.

As shown in FIG. 14, the two fasteners 60, 60' are retained by either the side of the slotted aperture insert and the end of the slotted aperture. The slotted aperture insert has beveled openings 118 and the fastener heads 191, 191' have head threads 193, 193' that cut into the beveled opening portion of the multiple fastener slotted aperture insert. The fasteners 60, 60' have bone threads 195, 195' on the distal ends that secure the fastener to the distal compact bone 72. The multiple fastener slotted insert 115 is secured in a single slotted fastener aperture 47 of the first wing. A press-slot 200 extends down from a top surface of the fastener divider 123 to allow compression of the fastener divider for press fitting the slotted aperture insert 116 into a slotted aperture of the bone plate.

Figure 15:
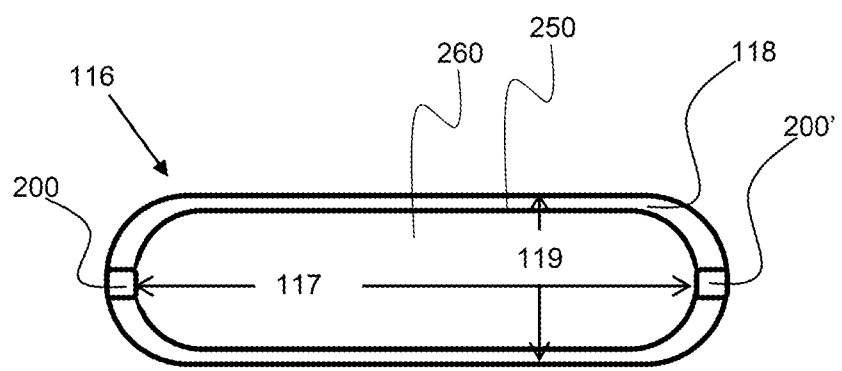
FIG. 15 shows a top view of an exemplary slotted aperture insert having a flange and a beveled opening.
Figure 16:
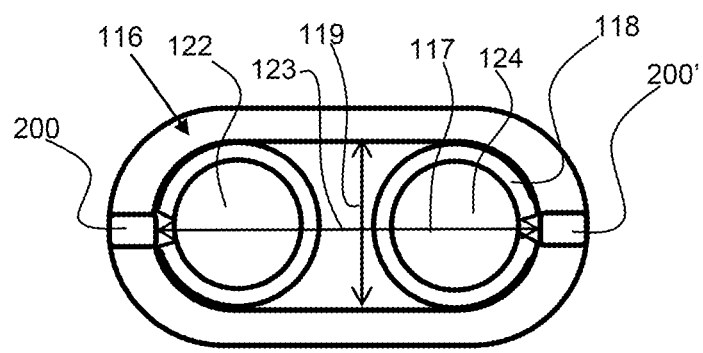
FIG. 16 shows a top view of an exemplary slotted aperture insert having fastener divider.

Referring now to FIG. 15, an exemplary slotted aperture insert 116 has a top surface 250 and a beveled opening 118 extending from the top surface of the slotted aperture 260. The slotted aperture has a width 119 from side to side and a length 117 from a first end to a second end. A pair of press-slots 200, 200' extend down from a top surface of the fastener divider 123 to allow compression of the fastener divider for press fitting the slotted aperture insert 116 into a slotted aperture of the bone plate As shown in FIG. 16, an exemplary slotted aperture insert 116 has a fastener divider 123 configured across the sides of the slotted aperture 260 to provide more area for the head of a fastener to cut therein. The divider forms a first fastener aperture 122 and a second fastener aperture 124 within the slotted aperture insert. A pair of press slots 200, 200' are configured on the ends of the slotted aperture insert 116.

A directional aperture may be configured in any suitable location on a load sharing bone plate, as described herein, to secure the bone plate to the bone. A directional aperture may be configured in any suitable location on a load sharing bone plate, as described herein, to secure the bone plate to the bone.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. An augmented spanning fixation bone plate assembly comprising:
   a) a spanning fixation bone plate comprising:
      a first end having an aperture therethrough;
      a second end having an aperture therethrough;
      a body portion configured between said first end and said second end and comprising:
         a top surface;

side surfaces;
a bone contacting surface;
wherein the spanning fixation bone plate extends a length along a length axis from said first end to said second end;
wherein a first fastener extends through the aperture in the first end to permit attachment of the first end to a first bone and wherein a second fastener extends through the aperture in the second end to permit attachment of the second end to a second bone; and b) an augmentation fixation bone plate detachably attached to the spanning fixation bone plate and comprising:
i) a length from a first end to a second end;
ii) an attachment portion having a retention aperture forming an interface surface that retains the augmentation fixation bone plate on the spanning fixation bone plate,
wherein the retention aperture is a through aperture forming a closed opening in the attachment portion;
iii) a first wing extending from the attachment portion to said first end of said augmentation fixation bone plate and having a bone contacting surface and a fastener aperture;
wherein the first wing extends laterally from the length axis of the spanning fixation bone plate to the first end of the augmentation fixation bone plate;
wherein the retention aperture extends around the spanning fixation bone plate;
wherein the augmentation fixation bone plate is configured to slidably engage with the body portion of the spanning fixation bone plate; and
wherein a fastener extends through the fastener aperture of the first wing to permit attachment of the first wing to a third bone that is a different bone from the first or second bone.

2. The augmented spanning fixation bone plate assembly of claim 1, wherein the fastener aperture in the first wing has an insert configured therein.

3. The augmented spanning fixation bone plate assembly of claim 2, wherein the insert in the fastener aperture of the first wing is a polymeric material.

4. The augmented spanning fixation bone plate assembly of claim 1, wherein the fastener aperture in the first wing is a slotted fastener aperture.

5. The augmented spanning fixation bone plate assembly of claim 4, wherein the slotted fastener aperture in the first wing has a multiple fastener slotted insert configured therein.

6. The augmented spanning fixation bone plate assembly of claim 5, wherein the multiple fastener slotted insert in the first wing has a fastener divider.

7. The augmented spanning fixation bone plate assembly of claim 1, wherein the attachment portion further comprises an insert opening to the retention aperture.

8. The augmented spanning fixation bone plate assembly of claim 7, wherein the insert opening is configured on the bone contacting surface of the augmentation fixation bone plate.

9. The augmented spanning fixation bone plate assembly of claim 8, wherein the retention aperture forms a flexure portion between the retention aperture and a top of the augmentation fixation bone plate that has a thickness that is no more than half a thickness of the augmentation fixation bone plate, wherein the augmentation fixation bone plate is configured to flex to expand the insert opening to extend over the spanning fixation bone plate.

10. The augmented spanning fixation bone plate assembly of claim 9, wherein the augmentation fixation bone plate is made of a polymeric material and the spanning fixation bone plate is made of a metal.

11. The augmented spanning fixation bone plate assembly of claim 1, wherein the augmentation fixation bone plate is made of a polymeric material and the spanning fixation bone plate is made of a metal.

12. The augmented spanning fixation bone plate assembly of claim 1, wherein the first wing extends laterally within 4 mm of the bone contacting surface of the spanning fixation bone plate.

13. The augmented spanning fixation bone plate assembly of claim 12, wherein the second wing extends laterally within 4 mm of the bone contacting surface of the spanning fixation bone plate.

14. The augmented spanning fixation bone plate assembly of claim 1, wherein the retention aperture comprises a ball and detent interface surface comprising a ball and detent to retain the spanning fixation bone plate to the augmented spanning fixation bone plate.

15. The augmented spanning fixation bone plate assembly of claim 1, wherein the bone contacting surface of the first wing is in planar alignment with the bone contacting surface of the spanning fixation bone plate.

16. The augmented spanning fixation bone plate assembly of claim 1, wherein the augmentation fixation bone plate further comprises:
a second wing extending from the attachment portion to said second end of said augmentation fixation bone plate and having a bone contacting surface and a fastener aperture;
wherein the second wing extends laterally from the length axis of the spanning fixation bone plate to the second end of the augmentation fixation bone plate; and
wherein a fastener extends through the fastener aperture of the second wing to permit attachment of the second wing to said third or a fourth bone that is a different bone from the first or second bone.

17. The augmented spanning fixation bone plate assembly of claim 16, wherein the bone contacting surface of the second wing is in planar alignment with the bone contacting surface of the spanning fixation bone plate.

18. The augmented spanning fixation bone plate assembly of claim 16, wherein the fastener aperture in the second wing has an insert configured therein.

19. The augmented spanning fixation bone plate assembly of claim 18, wherein the fastener aperture in the second wing is a slotted fastener aperture.

20. The augmented spanning fixation bone plate assembly of claim 19, wherein the slotted fastener aperture in the second wing has a multiple fastener slotted insert configured therein.

* * * * *